United States Patent [19]

Malo et al.

[11] Patent Number: 5,653,716
[45] Date of Patent: Aug. 5, 1997

[54] SUTURE MANIPULATING INSTRUMENT WITH GRASPING MEMBERS

[75] Inventors: Cheryne M. Malo, Attleboro, Mass.; Ronald P. Karzel, Northridge, Calif.

[73] Assignee: Acufex Microsurgical, Inc., Mansfield, Mass.

[21] Appl. No.: 365,651

[22] Filed: Dec. 29, 1994

[51] Int. Cl.$^6$ .................................................. A61B 17/04
[52] U.S. Cl. ........................... 606/139; 606/110; 606/113; 606/146
[58] Field of Search ........................ 606/110, 113, 606/148, 144, 146, 106, 139; 604/63

[56] References Cited

U.S. PATENT DOCUMENTS

| | | | |
|---|---|---|---|
| 797,183 | 8/1905 | Davis | 604/63 |
| 842,631 | 1/1907 | Deperdussin | 604/63 |
| 4,043,323 | 8/1977 | Komiya | 128/4 |
| 4,174,715 | 11/1979 | Hasson | 128/321 |
| 4,493,319 | 1/1985 | Polk et al. | 128/303 A |
| 4,890,615 | 1/1990 | Caspari et al. | 606/146 |
| 4,923,461 | 5/1990 | Caspari et al. | 606/146 |
| 4,935,027 | 6/1990 | Yoon | 606/146 |
| 5,201,740 | 4/1993 | Nakao et al. | 606/113 |
| 5,201,741 | 4/1993 | Dulebohn | 606/113 |
| 5,209,747 | 5/1993 | Knoepfler | 606/16 |
| 5,222,977 | 6/1993 | Esser | 606/223 |
| 5,250,054 | 10/1993 | Li | 606/148 |
| 5,258,005 | 11/1993 | Christian | 606/205 |
| 5,281,236 | 1/1994 | Bagnato et al. | 606/139 |
| 5,281,237 | 1/1994 | Gimpelson | 606/144 |
| 5,312,423 | 5/1994 | Rosenbluth et al. | 606/148 |
| 5,364,410 | 11/1994 | Failla et al. | 606/139 |

FOREIGN PATENT DOCUMENTS

WO 95/02998   2/1995   WIPO ................ A61B 17/04

OTHER PUBLICATIONS

Semm, K.; "Endoscopic Appendectomy", Endoscopy 15 (1983) 59–64.

Tsuchida, Seigi; From the Department Urology,Akita University School of Medicine, Akita, Japan; "A New Operative Fiberpyeloscope", Accepted for publication Jul. 2, 1976; Read at annual meeting of American Urological Association, Las Vegas, Nevada, May 16–20, 1976, 2 pp.

Brochure: Product Focus, Ideal Suture Grasper, "Introducing Versatility, Speed and Convenience to Arthroscopic Suturing", ID™ Innovasive® Devices, Inc., Nov. 1994 9000x116 Rev. A.

Brochure: "Handling Surgical Innovation", ID™ Innovasive Devices, Inc., ©1994 Innovasive Devices, Inc., Part No. 90000002 Rev. A., 4 pp.

Brochure: Instrument Makar, Inc., "Arthroscopic Products you won't find anywhere else.", 2 pp. 1986.

Brochure: Linvatec, "Maximize Your options.", ©1993 Linvatec Corporation, 1 page.

Surgical Products, Nov. 1992, p. 24.

*Primary Examiner*—Gary Jackson
*Attorney, Agent, or Firm*—Fish & Richardson, P.C.

[57] ABSTRACT

A surgical instrument an outer hollow member having a passageway extending therethrough. A handle is disposed near its proximal end to enable manipulation of the outer member. An inner movable assembly reciprocates through the passageway. A distal end of the inner assembly is drivable distally through the passageway from a retracted position to an extended position protruding distally beyond the distal end of the outer member. The distal end of the inner assembly terminates in at least first and second grasper members for traveling past and on either side of a portion of a surgical filament in the extended position and for encircling the filament portion in the retracted position to manipulate the filament within the patient.

28 Claims, 3 Drawing Sheets

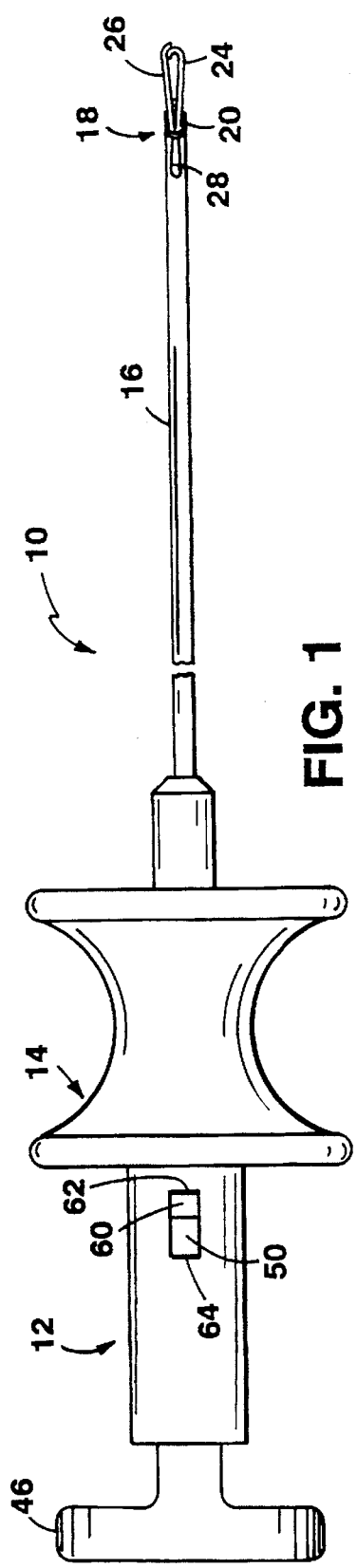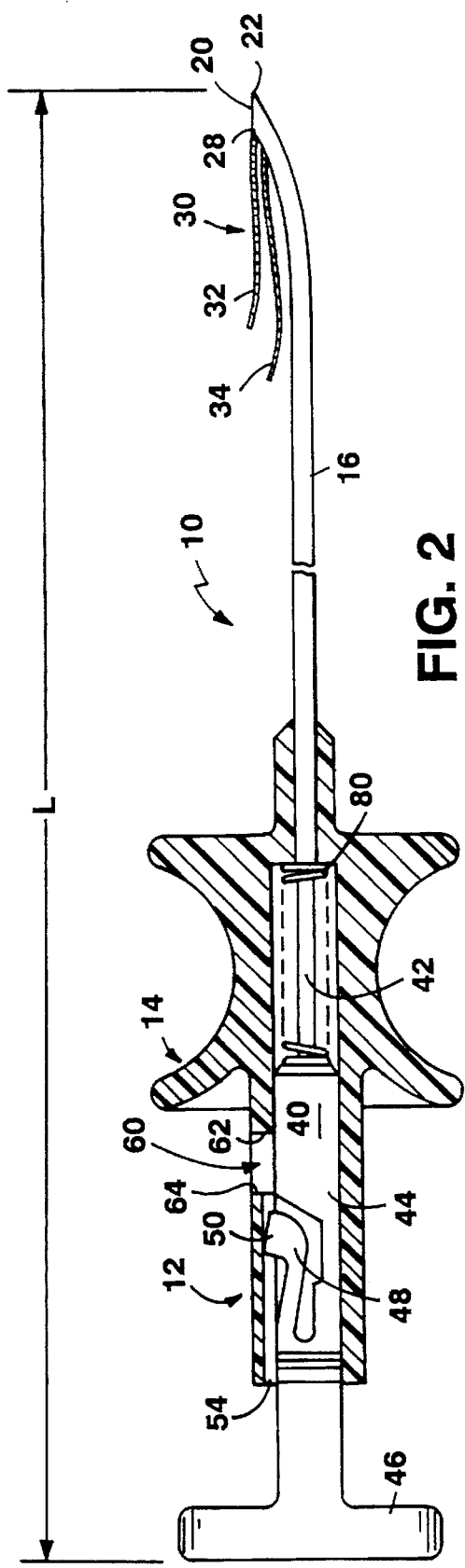

SUTURE MANIPULATING INSTRUMENT WITH GRASPING MEMBERS

FIELD OF THE INVENTION

This invention relates to instruments for suturing tissues and more particularly to a device which passes or retrieves a suture within a patient.

BACKGROUND OF THE INVENTION

Sutures are widely used within patients to secure two or more layers of soft tissue together, or to secure soft tissue to bone. During open procedures in which a large incision provides ready access to the tissues, surgeons have little difficulty in passing suture to the surgical site and then retrieving or withdrawing the suture to provide two free ends on either side of the tissue. The two ends of suture thereafter are knotted, or utilized for additional suturing of the tissue.

There are an increasing number of closed procedures conducted through one or more cannulas. Access to tissues is provided through narrow passageways within the cannulas. During some endoscopic and arthroscopic procedures, suture is delivered through a first cannula using an elongated needle and threaded through one side of the tissue. Thereafter, the suture must be retrieved through a second cannula using narrow grasper-type forceps or an elongated hollow suture retriever having an internal wire loop. The wire loop is extendable beyond the tip of the retriever to capture a free end of the suture. While graspers can grab a middle portion of a suture, the wire loop of the suture retriever can only be passed around a free end of the suture. Therefore, two or more instruments typically are required to perform endoscopic or arthroscopic suturing.

Several devices having an eye or groove for placing a suture through tissue are disclosed in U.S. Pat. No. 5,222,977 (Esser) and U.S. Pat. No. 5,281,237 (Gimpelson). Other instruments which deliver suture internally through the instrument, and methods of using same, are disclosed in U.S. Pat. No. 4,923,461 (Caspari, et al.) and U.S. Pat. No. 4,935,027 (Yoon), for example.

Instruments with two or more grasping elements are presently used in other surgical fields such as for retrieving gall stones. In nonsurgical fields, object retrievers are sold in certain hardware stores for retrieving screws, nuts and other items. Also available are pickle tongs having three or four wires which are protrudable to grasp a pickle from a jar.

SUMMARY OF THE INVENTION

Therefore, it is an object of the present invention to provide an improved, versatile suture manipulating instrument which provides multiple suturing functions within a patient.

It is a further object of this invention to provide such an instrument which can pierce soft tissue to pass suture or other surgical filament through the tissue.

Yet another object of this invention is to provide such instrument which can grasp and then withdraw a middle portion of a suture to retrieve it from the body.

A still further object of this invention is to provide an improved suture manipulating instrument which selectively enables relative movement between a surgical filament and the instrument or firmly captures the filament to prevent relative movement during passing or retrieval of the filament through tissue.

This invention features a surgical instrument having an outer hollow member having a passageway extending therethrough. A handle is disposed near its proximal end for enabling manipulation of the outer member. An inner movable assembly reciprocates through the passageway. A distal end of the inner assembly is drivable distally through the passageway from a retracted position to an extended position protruding distally beyond the distal end of the outer member. The distal end of the inner assembly terminates in at least first and second grasper members for traveling past and on either side of a portion of a surgical filament in the extended position and for encircling the filament portion in the retracted position to enable manipulation of the filament within the patient.

In one embodiment, the first and second grasping members are formed of resilient wires, one of which terminates distally in a curved, hook-like element. The proximal end of the inner assembly defines a handle element to which a first force is applied to drive the distal end of the inner assembly to the extended position, and the instrument further includes a spring element which biases the inner assembly toward the retracted position by providing a second force. The inner assembly further includes a locking element having a resilient arm defining a detent which is releasably received by a recess in the handle. The recess includes a proximal guide channel defined by the handle along which detent is linearly slidable to guide reciprocation of the inner assembly and to inhibit its rotation. The recess further includes a lock opening at the distal end of the guide channel which communicates between the passageway and the exterior of the handle to receive the detent of the resilient arm when the inner assembly is in the extended position.

In a preferred embodiment, the distal end of the inner assembly rests fully within the passageway in the retracted position for drawing the encircled filament portion at least partially into the passageway to restrict relative movement between the filament and the instrument, and the instrument further includes an intermediate position in which the first and second grasping members encircle the filament portion but enable relative movement between the filament and the instrument. The detent of the resilient arm has a leading surface and a trailing surface, and the handle defines the lock opening as an elongated port having a distal edge and a proximal edge such that the leading surface of the detent rests against the port's distal edge in the extended position and the trailing surface rests against the port's proximal edge in the intermediate position.

The distal end of the instrument preferably terminates in a sharp distal tip for penetrating tissue. The distal end is curved upwardly so that its distal opening faces laterally and the distal tip projects longitudinally. A longitudal slot opens distally into the distal opening and extends proximally therefrom. The longitudal slot has a width sufficient to accommodate the encircled filament portion, especially during passing of the filament through tissue.

BRIEF DESCRIPTION OF THE DRAWINGS

Other objects, features and advantages will occur from the following description of preferred embodiments and the accompanying drawings, in which:

FIG. 1 is a top view of a suture manipulating instrument according to the present invention in an intermediate position;

FIG. 2 is a side, partial cross-sectional view of the instrument of FIG. 1 in a retracted position;

DETAILED DESCRIPTION OF THE PREFERRED EMBODIMENTS

Figure 3A:
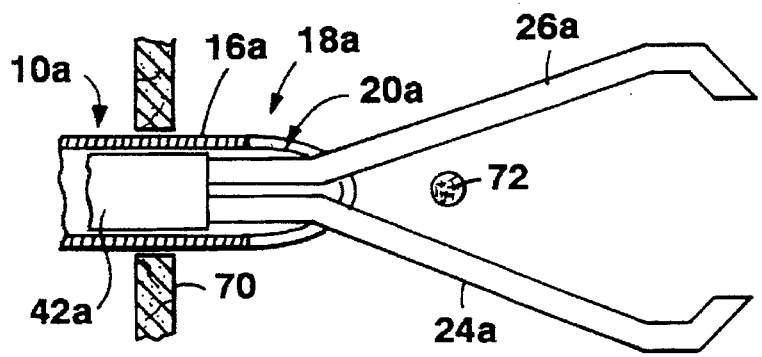
FIGS. 3A–3C show an alternative suture manipulating instrument retrieving suture through tissue.

This invention may be accomplished by a suture management instrument 10, FIGS. 1 and 2, having an outer hollow member 12 with an integral handle 14 and an elongated needle 16 which terminates in a distal end 18. A passageway 20 through needle 16 terminates with a distal opening 20. As best shown in FIG. 2, the distal portion of the needle 16 curves upwardly such that distal opening 20 faces laterally while a sharp tip 22 projects longitudally relative to the instrument 10.

A pair of grasping members 24, 26 extend beyond the distal end 18 in the intermediate position shown in FIG. 1. The needle 16 further defines a longitudal suture slot 28 which terminates at its distal end with the distal opening 20. As shown in FIG. 2, a portion of filament 30 is carriable by the instrument 10 in a retracted position such that filament legs 32, 34 extend from the slot 28. This configuration is particularly useful for passing suture or other surgical filament into and through tissue as described in relation to FIGS. 3A–3C below. The term "filament" encompasses all types of sutures including monofilaments, tapes and braided ribbons.

Figure 4:
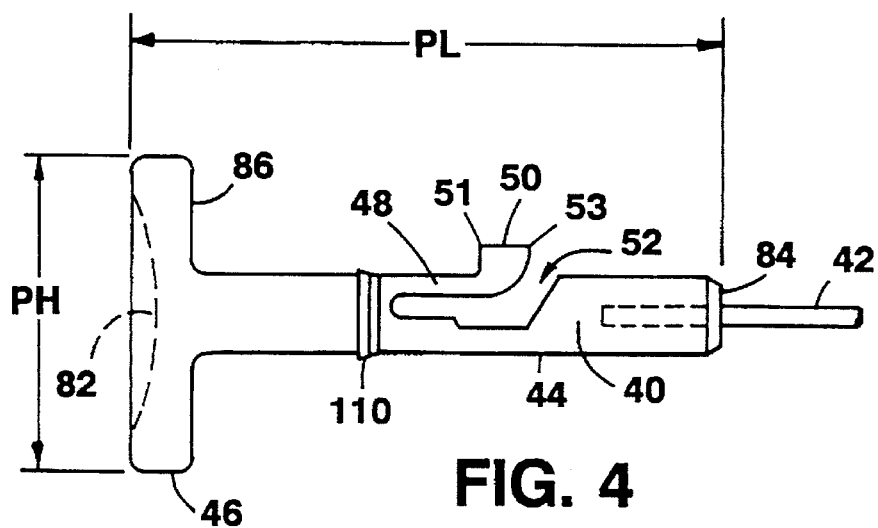
FIG. 4 is a side view of the proximal portion of the inner assembly of FIGS. 1 and 2.
Figure 6:
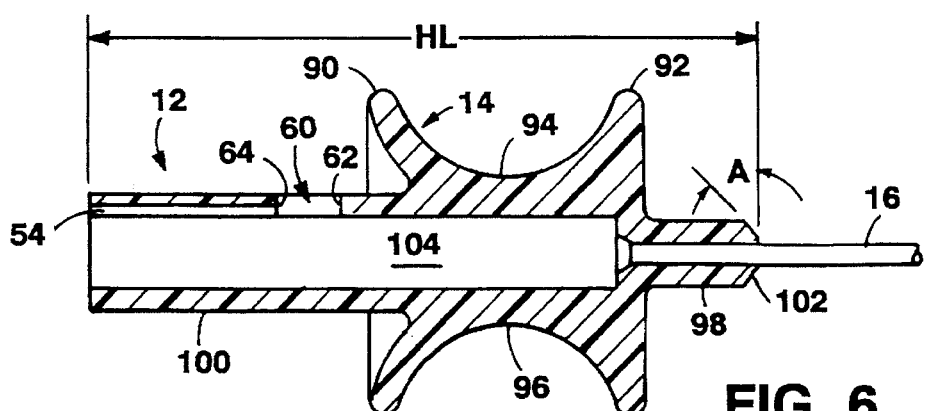
FIG. 6 is a side cross-sectional view of the proximal portion of the outer assembly shown in FIG. 2.

The suture management instrument 10 further includes an inner moveable assembly 40 having an elongated element 42 which terminates in grasping members 24, 26. As shown in FIGS. 2 and 4, the element 42 is embedded in a plunger 44 which terminates at its proximal end in an enlarged head or handle 46. In its central portion, the plunger 44 has a resilient arm 48 which terminates in a laterally projecting detent 50. The arm 48 deforms into a cavity 52 in the retracted position as shown in FIG. 2 to travel in a proximal guide channel 54. As shown in FIGS. 2 and 6, the handle 14 defines the proximal guide channel 54 which in turn communicates at its distal end with a lock opening 60. The channel 54 guides longitudal reciprocation of the inner assembly 40 and inhibits relative rotation between the assembly 40 and the outer hollow member 12. The channel 54 also enables to detent 50 to have a larger height than the inner diameter of the handle 14 which therefore enables the detent 50 to both key into the channel 54, FIG. 2, and project into the lock opening 60, FIG. 1.

As shown in FIGS. 1, 2 and 6, the lock opening 60 is an elongated port having a leading edge 62 and a trailing edge 64. The detent 50 rests against the trailing edge 64 in the intermediate position showing FIG. 1 and rests against the leading edge 62 in an extended position.

Figure 3B:
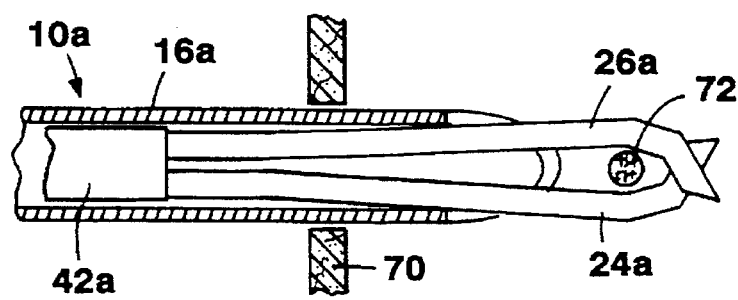
Figure 3C:
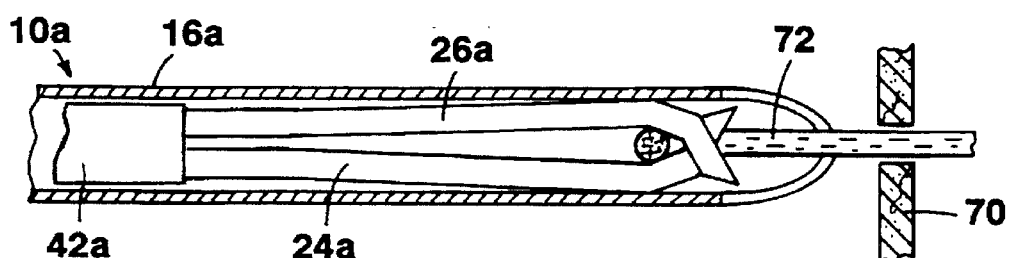

The extended, intermediate and retracted positions are shown in FIGS. 3A–3C, respectively, for an alternative suture management instrument 10a having a straight needle 16a with slanted distal opening 20a. The needle 16a is shown in FIG. 3A with its distal end 18a piercing and extending through soft tissue 70. Symmetrical grasping members 24a, 26a are shown in an extended position passing on either side of a surgical suture 72. The extended position is maintained by continuous exertion of a first manual force against first surface 82, FIG. 4, to overcome the second biasing force of spring 80, FIG. 2.

During retrieval, the first manual force is discontinued, which allows spring 80 to drive the inner element 42a of the inner assembly proximally to draw symmetrical grasping members 24a, 26a partially within the distal end 18a. A camming effect against the rim of distal opening 20a forces the grasping members 24a, 26a toward each other to encircle the suture 72 in an intermediate position. In one procedure, the instrument 10a is withdrawn while in the intermediate position to enable relative movement between the suture 72 and the grasping members 24a, 26a. This procedure is especially useful when it is desired to access one end of the suture 72 while leaving the remainder of the suture 72 on the far side of the tissue 70.

In an alternative retrieval procedure, the inner element 42a is further withdrawn manually into a retracted position while the needle 16a protrudes through the tissue 70. Relative movement between the suture 72 and the instrument 10a is thereby inhibited, and the captured portion of the suture 72 is thereafter withdrawn through the tissue 70 as shown in FIG. 3C. Both legs of the suture 72 on either side of the captured portion are therefore withdrawn simultaneously through the tissue 70.

The retracted position is particularly useful during passing or delivery of a suture through tissue. The suture slot 28, FIG. 2, in the distal end 18 enables the legs 32, 34 of the suture 30 to easily follow behind the sharp edge 22 while presenting a low profile. Further, the suture 30 while within the slot 28 avoids damage by contact which might otherwise occur with sharp edges surrounding the distal opening 20, or by abrasion against tissue or other instruments. The tissue penetration ability of distal end 18 also remains unencumbered by suture 30 when it rests in slot 28.

The inner assembly 40, FIG. 2, is biased toward the retracted position by a spring 80. The inner assembly 40 is driven to the intermediate or extended positions by applying pressure to a first, concave surface 82, FIG. 4, to counteract the biasing force applied to a second surface 84 behind the spring 80. A second, proximal force is applied manually to surface 86 of the plunger handle 46 to pull the inner assembly 40 from the intermediate position to the retracted position by overcoming the resistance provided by detent 50 against distal edge Alternatively, the detent 50 has a greater height to protrude above the upper surface of the recess 60 to enable manual depression of the detent 50, which provides push-button release of the inner assembly In one construction, the instrument 10 has an overall length L, FIG. 2, of 9.3 inch in the retracted position. With the plunger 44 fully depressed, the tips of asymmetric grasping members 24, 26 protrude approximately 0.37–0.44 inch beyond the end of the needle 16. The proximal guide channel 54 has a width of approximately 0.12 inch and a longitudal length of 0.66 inch. The lock opening 60 has a length of 0.38 inch and a width of 0.12 inch. The handle 14 and the plunger 44 are formed of DELRIN polyacetal or NYLON polymer. The needle 16 has a total length of approximately 6.6 inch, of which the proximal 0.6 inch is embedded within the plunger 44 as shown in FIG. 4, and 0.7 inch of the distal end of the needle 16 curves upwardly by approximately 0.29 inch. The needle 16 is 304 stainless steel 14 TW hypodermic tubing having an outer diameter of 0.07–0.09 inch, preferably 0.083 inch, and an inner diameter of 0.067 inch. The suture slot 28, FIG. 1, has a length of 0.1 inch and a width of 0.03 inch with radiused edges to avoid damage to suture.

Figure 7:
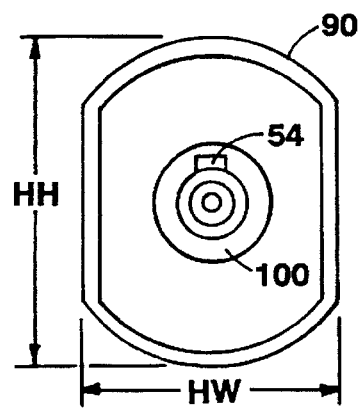
FIG. 7 is a rear end view of the outer assembly shown in FIG. 6.

The proximal end of outer hollow member 12, FIGS. 6 and 7, has a length HL of 2.6 inch, a maximum handle height HH of 1.2 inch and a width HW of 1 inch. Handle 14 has rims 90, 92 which provide a convenient grip of the instrument 10 for the surgeon by using the index and middle finger resting upon upper and lower surfaces 94, 96, respectively. Distal cylinder 98 and proximal cylinder 100 are integrally formed with the handle 14. Distal cylinder 98 has an outer diameter of approximately 0.25 inch and secures the proximal end of needle 16 therein. A leading surface 102 of the cylinder 98 is chamfered at angle A of approximately 40 degrees.

Proximal cylinder 100 has an outer diameter of 0.45 inch and an inner diameter of 0.28 inch. The cylinder 100 defines an inner cavity 104 which receives the plunger portion 44, FIG. 4. The plunger 44 has an overall length PL of 1.98 inch and handle 46 has a height PH of 1 inch. In this construction, plunger handle 46 is a circular button-type handle. Alternatively, a finger loop or other type of handle can be utilized.

Plunger 44 is centered within cavity 104, FIG. 6, by ribs 110, FIG. 4. Trailing surface 51 of detent 50 is perpendicular in this construction, but alternatively is chamfered at a 45 degree angle to assist unlocking of the detent during transition from the intermediate position to the retracted position. Leading surface 53 has a perpendicular upper surface which then curves gradually to the underside of arm 48.

Figure 5:
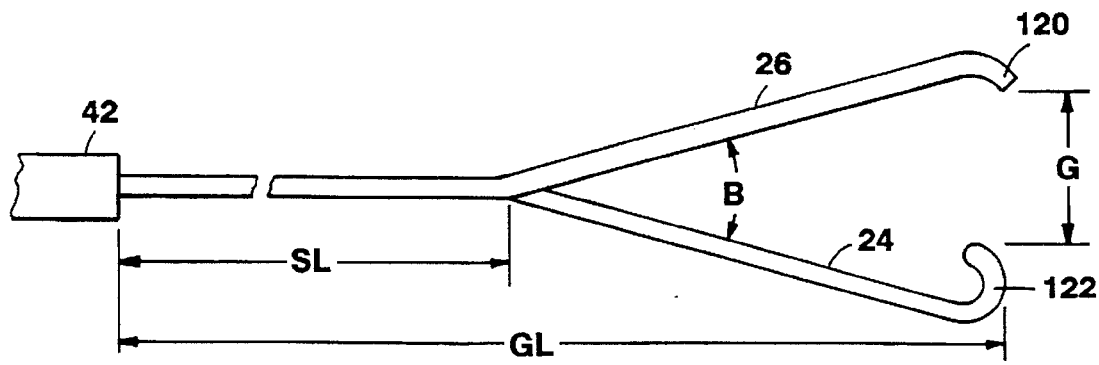
FIG. 5 is an enlarged top view of the distal end of the inner assembly and grasping members of the instrument of FIG. 1.

Element 42 is a hollow tube formed of 304 stainless steel having an outer diameter of 0.058 inch and an inner diameter 0.048 inch, and a length of 6.7 inch. The proximal end of grasper members 24, 26, FIG. 5, are crimped into the distal end of the tubular element 42. Grasper members 24, 26 are formed of 0.018 diameter 302 spring tempered stainless steel music wire having an overall length of approximately 1.16 inch. When crimped in the end of element 42, the wires 24, 26 have a straight length SL of 0.55 inch and a total projecting length GL of 1 inch. A gap G of 0.11–0.15 inch is maintained in the extended position shown in FIG. 5. Grasping wires 24, 26 form an angle B of approximately 30 degrees. Grasper tip 122 is curved back upon itself to assist snagging of a suture, while tip 120 is only slightly curved to facilitate disengagement when a suture is being separated or released from the instrument 10. Alternatively, grasper members 24, 26 are formed from a single, U-shaped wire whose central portion is secured to the element 42.

In this construction, spring 80, FIG. 2, is formed of 302 stainless steel with a spring temper, such catalog number C0180-020-0880-S available from Associated Spring in Bristol, Conn. The spring 80 has an outer diameter of 0.18 inch, a wire diameter of 0.02 inch, a free length of 0.8 inch and, when compressed, a solid height of 0.27 inch. The spring rate, which provides the second, biasing force, is approximately 4.4 lb/in.

Although specific features of the invention are shown in some drawings and not in others, this is for convenience only as each feature may be combined with any or all of the other features in accordance with the invention.

Other embodiments will occur to those skilled in the art and are within the following claims.

What is claimed is:

1. A surgical instrument for manipulating a surgical filament within a patient, comprising:

an outer hollow member having a proximal end, a distal end, and a passageway extending between said proximal and distal ends;

a handle disposed on said outer member near said proximal end for enabling manipulation of said outer member;

an inner movable assembly for reciprocating through said passageway and having a proximal end and a distal end, said proximal end defining a first surface to which a first force is applied to drive said distal end of said inner assembly distally through said passageway from a retracted position to an extended position protruding distally beyond said distal end of said outer member;

said inner assembly further defining a second surface to which a second force is applied to drive said inner assembly from said extended position to said retracted position; and said distal end of said inner assembly terminating in at least first and second grasping members for traveling past and on either side of a portion of the filament in said extended position and for encircling the filament portion in said retracted position to enable manipulation of the filament within the patent, wherein at least one of said grasping members terminates distally in a curved, hook-like element.

2. The surgical instrument of claim 1 wherein each of said first and second grasping members are formed of a resilient wire.

3. The surgical instrument of claim 1 further including means, coupled between said inner movable assembly and said outer member, for providing said second force to return said inner assembly to said retracted position.

4. The surgical instrument of claim 3 in which said means for providing the second force is a spring element which biases said inner assembly toward said retracted position.

5. The surgical instrument of claim 1 in which said proximal end of said inner assembly defines a handle element to which the first force is applied.

6. The surgical instrument of claim 1 in which said inner assembly further includes a locking element for interacting with a corresponding element defined by said handle.

7. The surgical instrument of claim 6 in which said locking element is a resilient arm positionable within said passageway and said corresponding element is a recess communicating with said passageway for releasably receiving a detent defined by said resilient arm.

8. The surgical instrument of claim 7 in which said recess includes a proximal guide channel defined by said handle along which said detent is linearly slidable to guide reciprocation of said inner assembly and to inhibit rotation, and further includes a lock opening defined by said handle at the distal end of said guide channel, said lock opening communicating between said passageway and the exterior of said handle to receive said detent when said inner assembly is in said extended position.

9. The surgical instrument of claim 8 in which said distal end of said inner assembly rests fully within said passageway in said retracted position for drawing the encircled filament portion at least partially into said passageway to restrict relative movement of the filament and said instrument, and said instrument further includes an intermediate position in which said first and second grasping members encircle the filament portion but enable relative movement of the filament.

10. The surgical instrument of claim 9 in which said detent has a leading surface and a trailing surface and said handle defines said lock opening as an elongated port having a distal edge and a proximal edge such that said leading surface of said detent rests against said distal edge in said extended position and said trailing surface rests against said proximal edge in said intermediate position.

11. The surgical instrument of claim 1 in which said distal end of said outer hollow member terminates in a sharp distal tip for penetrating tissue, said distal end further defining a distal opening.

12. The surgical instrument of claim 11 in which said distal end of said outer hollow member is curved upwardly so that said distal opening faces laterally and said distal tip projects longitudinally.

13. The surgical instrument of claim 11 in which said distal end further of said outer hollow member defines a longitudinal slot opening distally into said distal opening and extending proximally therefrom, and having a width sufficient to accommodate the encircled filament portion.

14. A surgical instrument for manipulating a surgical filament within a patient, comprising:

an outer hollow member having a proximal end, a distal end, and a passageway extending between said proximal and distal ends, said distal end terminating in a sharp distal tip for penetrating tissue;

a handle disposed on said outer member near said proximal end for enabling manipulation of said outer member;

an inner movable assembly for reciprocating through said passageway and having a proximal end and a distal end, said proximal end defining a first surface to which a first force is applied to drive said distal end of said inner assembly distally through said passageway from a retracted position fully within said passageway to an extended position protruding distally beyond said distal end of said outer member;

said inner assembly further defining a second surface to which a second force is applied to drive said inner assembly from said extended position to said retracted position; and said distal end of said inner assembly terminating in at least first and second grasping members for traveling past and on either side of a portion of the filament in said extended position and for encircling the filament portion in said retracted position to enable manipulation of the filament within the patient, each of said first and second grasping members being formed of a resilient wire.

15. The surgical instrument of claim 14 wherein at least one of said grasping members terminates distally in a curved, hook-like element.

16. The surgical instrument of claim 14 further including means, coupled between said inner movable assembly and said outer member, for providing said second force to return said inner assembly to said retracted position.

17. The surgical instrument of claim 16 in which said proximal end of said inner assembly defines a handle element to which the first force is applied.

18. The surgical instrument of claim 17 in which said handle element terminates proximally in an enlarged head.

19. The surgical instrument of claim 17 in which said inner assembly further includes a locking element for interacting with a corresponding element defined by said handle, said locking element being a resilient arm positionable within said passageway and said corresponding element being a recess communicating with said passageway for releasably receiving a detent defined by said resilient arm.

20. The surgical instrument of claim 19 in which said recess includes a proximal guide channel defined by said handle along which said detent is linearly slidable to guide reciprocation of said inner assembly and to inhibit rotation, and further includes a lock opening defined by said handle at the distal end of said guide channel, said lock opening communicating between said passageway and the exterior of said handle to receive said detent when said inner assembly is in said extended position.

21. The surgical instrument of claim 20 in which said distal end of said inner assembly rests fully within said passageway in said retracted position for drawing the encircled filament portion at least partially into said passageway to restrict relative movement of the filament and said instrument, and said instrument further includes an intermediate position in which said first and second grasping members encircle the filament portion but enable relative movement of the filament.

22. The surgical instrument of claim 21 in which said detent has a leading surface and a trailing surface and said handle defines said lock opening as an elongated port having a distal edge and a proximal edge such that said leading surface of said detent rests against said distal edge in said extended position and said trailing surface rests against said proximal edge in said intermediate position.

23. The surgical instrument of claim 22 in which said sharp distal tip for penetrating tissue defines a distal opening, and said distal end of said hollow outer member is curved upwardly so that said distal opening faces laterally and said distal tip projects longitudinally.

24. The surgical instrument of claim 23 in which said distal end of said hollow outer member further defines a longitudinal slot opening distally into said distal opening and extending proximally therefrom, and having a width sufficient to accommodate the encircled filament portion.

25. A surgical instrument for manipulating a surgical filament within a patient, comprising:

an outer hollow member having a proximal end, a distal end, and a passageway extending between said proximal and distal ends, said distal end terminating in a sharp distal tip for penetrating tissue, said outer member including a handle near said proximal end for enabling manipulation of said outer member;

an inner movable assembly for reciprocating through said passageway and having a proximal end and a distal end, said distal end of said inner assembly being drivable distally through said passageway from a retracted position to an extended position protruding distally beyond said distal end of said outer member; and said distal end of said inner assembly terminating in at least first and second grasping members for traveling past and on either side of a portion of the filament in said extended position and for encircling the filament portion in said retracted position to enable manipulation of the filament within the patient, each of said first and second grasping members being formed of a resilient wire.

26. A surgical instrument for manipulating a surgical filament within a patient, comprising:

an outer hollow member having a proximal end, a distal end, and a passageway extending between said proximal and distal ends, said outer member including a handle near said proximal end enabling manipulation of said outer member;

an inner movable assembly for reciprocating through said passageway and having a proximal end and a distal end, said distal end of said inner assembly being drivable distally through said passageway from a retracted position to an extended position protruding distally beyond said distal end of said outer member;

said distal end of said inner assembly terminating in at least first and second grasping members for traveling past and on either side of a portion of the filament in said extended position and for encircling the filament portion in said retracted position to enable manipulation of the filament within the patient, wherein said first grasping member is formed of a resilient wire; and said inner assembly includes a locking element and said handle includes a corresponding element cooperatively structured to retain said inner assembly at a fixed position relative to said outer hollow member.

27. The surgical instrument of claim 26, wherein said locking element and said corresponding element are cooperatively structured to retain said inner assembly at an intermediate position between said retracted position and said extended position.

28. A surgical instrument for manipulating a surgical filament within a patient, comprising:

an outer hollow member having a proximal end, a distal end, and a passageway extending between said proximal and distal ends, said outer member including a handle near said proximal end enabling manipulation of said outer member;

an inner movable assembly for reciprocating through said passageway and having a proximal end and a distal end, wherein said distal end of said inner assembly can be driven distally through said passageway from a retracted position to an extended position protruding distally beyond said distal end of said outer member; and said distal end of said inner assembly terminating in at least first and second grasping members for traveling past and on either side of a portion of the filament in said extended position and for encircling the filament portion in said retracted position to enable manipulation of the filament within the patient, wherein said first grasping member is formed of a resilient wire, and wherein said distal end of said outer member defines a longitudinal slot opening distally into said distal opening and extending proximally therefrom, and having a width sufficient to accommodate said encircled filament portion.

* * * * *

UNITED STATES PATENT AND TRADEMARK OFFICE
CERTIFICATE OF CORRECTION

PATENT NO. : 5,653,716

DATED : August 5, 1997

INVENTOR(S) : Cheryne M. Malo et al.

It is certified that error appears in the above-identified patent and that said Letters Patent is hereby corrected as shown below:

Col. 4, line 40, after "edge" insert --64.--.

Col. 4, line 43, after "assembly" insert --40.--.

Signed and Sealed this

Twenty-seventh Day of October, 1998

*Attest:*

BRUCE LEHMAN

*Attesting Officer*     *Commissioner of Patents and Trademarks*